United States Patent [19]

Campbell et al.

[11] Patent Number: 5,121,340
[45] Date of Patent: Jun. 9, 1992

[54] MULTI-LEVEL PROBE AND SYSTEM FOR MEASUREMENT OF PHYSICAL CONDITIONS IN LIQUID-CONTAINING TANKS

[75] Inventors: Eric Campbell, Logan, Utah; Gaylon Campbell, Pullman, Wash.; Jeff Norton; Art Heers, both of Logan, Utah

[73] Assignee: Campbell Scientific, Inc., Logan, Utah

[21] Appl. No.: 534,932

[22] Filed: Jun. 8, 1990

[51] Int. Cl.5 .................... G01S 15/00; G01N 29/14; G01N 29/22; G01N 29/24
[52] U.S. Cl. .................... 364/509; 73/1 H; 73/602; 73/290 V; 181/124; 181/402; 340/621; 364/556; 367/99; 367/151; 367/908
[58] Field of Search .............. 364/509, 510, 556, 561, 364/562, 564; 367/87, 99, 151, 902, 908, 48; 73/1 H, 602, 609, 861, 861.18, 861.28, 861.25, 290 V, 290 R; 340/612, 618, 621; 181/123, 124, 402

[56] References Cited

U.S. PATENT DOCUMENTS

| | | | |
|---|---|---|---|
| 2,787,160 | 4/1957 | Van Valkenburg | 367/908 X |
| 2,998,723 | 9/1961 | Smith, Jr. et al. | |
| 3,010,318 | 11/1961 | Mongan | 367/908 X |
| 3,184,968 | 5/1965 | Werner | 73/290 V |
| 3,214,974 | 11/1965 | Altman et al. | 367/908 X |
| 3,229,523 | 9/1965 | Boyd et al. | 73/290 V X |
| 3,372,592 | 3/1968 | Gravert | 367/908 X |
| 3,394,589 | 7/1968 | Tomioka | |
| 3,965,455 | 6/1976 | Hurwitz | 367/151 |
| 4,090,407 | 5/1978 | Shuler et al. | 73/290 V |
| 4,487,065 | 12/1984 | Carlin et al. | 73/290 V |
| 4,545,245 | 10/1985 | Sharp | 73/290 V |
| 4,598,742 | 7/1986 | Taylor | 364/509 X |
| 4,623,264 | 11/1986 | Mitchell | 73/1 H X |
| 4,748,846 | 6/1988 | Haynes | 73/290 V |
| 4,793,178 | 12/1988 | Ahern et al. | 73/290 V X |
| 4,928,525 | 5/1990 | Aderholt et al. | 364/509 X |
| 4,934,186 | 6/1990 | McCoy | 367/908 X |

FOREIGN PATENT DOCUMENTS 1205305 11/1965 Fed. Rep. of Germany.
1243497/18-- 10 3/1970 U.S.S.R. .

Primary Examiner—Parshotam S. Lall
Assistant Examiner—E. J. Pipala
Attorney, Agent, or Firm—Wells, St. John & Roberts

[57] ABSTRACT

A multi-level probe for sonic range measurements utilizes a plurality of parallel reflectors that each include an opening arranged coaxially about a beam of ultrasonic energy transmitted along a reference axis from an associated transducer. The opening in each reflector permits most of the sonic energy to pass to a subsequent reflective surface, while the periphery about the opening provides echo signals for determining physical conditions in the environment through which the sonic energy has passed. A novel system is used for determining physical conditions that are a function of time differences between signals from different reflectors, calculated with a highly efficient digital signal processing algorithm.

32 Claims, 3 Drawing Sheets

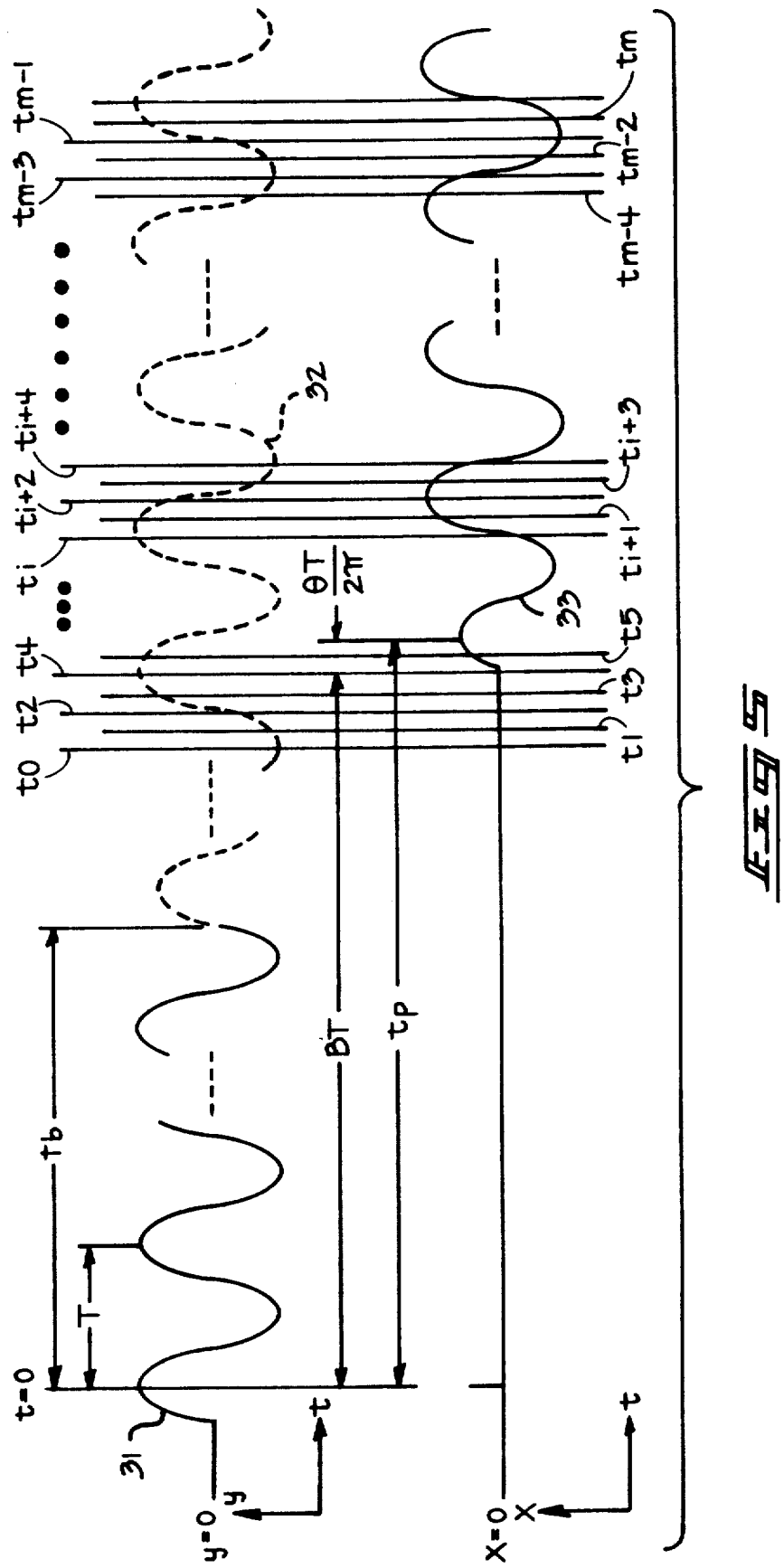

MULTI-LEVEL PROBE AND SYSTEM FOR MEASUREMENT OF PHYSICAL CONDITIONS IN LIQUID-CONTAINING TANKS

TECHNICAL FIELD

This disclosure pertains to apparatus and methods designed for usage within a liquid-containing tank for measuring physical conditions within the interior of the tank that are a function of the transit time of sonic energy through the liquid, such as liquid level, volume, density, and temperature.

BACKGROUND OF THE INVENTION

The present improvements were developed to provide users of underground liquid storage tanks with inventory and leak detection information. More specifically, they were developed to provide periodic reconciliation of product flow-through in liquid storage tanks, as well as leak detection during quiescent periods.

The use of sound energy has been proposed previously for measuring distances in a liquid by directing sound waves against reflective surfaces at known locations within the liquid and against the liquid surface. The reflection of such sound waves provides echoes which result in output signals that can be processed to measure liquid depth. When the sound waves are directed vertically within a liquid-containing tank, one can measure the liquid level within the tank, and thereby compute the volume of liquid at a selected time. Various systems for analyzing reflected signals to measure liquid level within a tank have been described in numerous U.S. patents, such as U.S. Pat. Nos. 2,787,160, 3,214,974, and 4,748,846.

A set of reference reflectors spaced vertically at known positions relative to a source of ultrasound energy within a liquid having known physical parameters will provide echoes whose differential timing correlates to the average temperature between the reflectors. However, when working over a vertical distance that demands a series of reflectors, the arrangement of conventional radial tabs or reflectors one above the other will cause the acoustic energy from the transducer to become attenuated by a shadowing effect. While it is recognized that the transmitted acoustic energy in the liquid does bend about each reflector due to a fringe effect, and that the reflectors can be focused and/or stepped to maximize the echo amplitude returned to the transducer, conventional configurations of reference reflectors as evidenced in the above-identified U.S. patents have been found to become limiting in many practical applications of this technology.

Monitoring of product flow-through and leak detection processes in liquid storage tanks requires accurate periodic measurement of liquid level and temperature changes that have occurred over the monitored time. Both the velocity of sound in a liquid and its density are affected by temperature changes that might have occurred. Volume comparisons of liquid at different times can be made by converting actual liquid volume to "net volume" (corrected to a reference temperature, such as 60° C.) or by correcting measured volume to the initial temperature conditions.

Changes in the liquid level that have occurred over the monitored period can be determined by periodic measurement of the transit time or propagation time of sonic energy reflected back to a transducer from the liquid surface. Relative temperature changes that have occurred in the liquid from one measurement time to the next can be determined by measurement of changes in the transit time of the sonic energy reflected back to the transducer from a series of reflectors at known heights throughout the liquid. This temperature information can then be used in calculating volume changes to reconcile flow-through over a period of tank usage or for leak detection over a quiescent period.

Many factors have been identified as contributing to possible errors in both liquid level or volume calculation and leak detection for liquid storage tanks. Effects of temperature on liquid density and sound velocity have the most significant impact. The probe disclosed herein provides a means for determining liquid level and volume, liquid density changes with time and relative densities and liquid temperatures at a substantial number of levels within a tank using periodic measurements of ultrasonic propagation velocity.

The speed of sound through a medium is a direct function of its density and modulus of elasticity. Since density varies with temperature, temperature can be indirectly determined by measuring the speed of sound through the liquid. Changes in density can be measured by determining changes in the propagational velocity of sound over a known distance in the liquid.

When liquid is added to a tank (for example, during a delivery), the temperature of the now-combined liquid in the tank will increase or decrease as it seeks thermal equilibrium with the surrounding environment—atmosphere, backfill, native soil and ground water—about the tank. Similarly, newly-introduced liquid will also seek thermal equilibrium with the liquid previously present in the tank. This equalization process generally has a long time constant and tends toward either thermal stratification or homogeneity, depending on the temperature differential of the two liquids and the surrounding environment.

As a result of developing a two dimensional thermal model of liquids within a tank, it has been determined that thermal knowledge of six inch horizontal sections of the product in a tank would provide adequate temperature information to apply as a correction factor when calculating net volume of the liquid in large storage tanks of the type used for petroleum products. The disclosed probe makes such accurate measurements of propagation time practical in large liquid storage tanks.

The present invention provides a novel probe wherein most of the acoustical energy passes through each reference reflector to subsequent reflectors, while assuring the reflection of an identifiable echo to the transducer. In addition, a novel processing system for the reflected output signals has been developed to effectively convert the reflected output signals to the transit time or propagation time of the reflected energy, which is a direct function of liquid density.

BRIEF DESCRIPTION OF THE DRAWINGS

The preferred embodiment of the invention is illustrated in the accompanying drawings, in which:

FIG. 5 is a plot of transmitted and reflected signals at the transducer.

DETAILED DESCRIPTION OF THE PREFERRED EMBODIMENT

The following disclosure of the invention is submitted in compliance with the constitutional purpose of the Patent Laws "to promote the progress of science and useful arts" (Article 1, Section 8).

Generically speaking, the following description pertains to measurement devices for determining physical conditions (liquid levels, temperature, density, volume, mass) within a liquid, specifically liquid contained within a tank. It operates on the principle of sonar. A burst of acoustic, high frequency energy is transmitted from a transducer fixed to a probe and located at the bottom of the tank. The transducer is aimed vertically upward through the liquid. Reference surfaces on the probe at known distances reflect this energy downward and produce echoes that can be detected by the transducer. In addition, the sound energy that reaches the liquid surface is also reflected downward. The reflected sound waves arrive at the transducer as an echo which can be amplified and digitized for data processing purposes.

In applications with high variability in sonic propagation rates due to temperature or other properties of the tank environment, accuracy in measurement of physical properties within the tank is directly related to the number of reference reflectors that can be placed in the path of the sound waves. When using conventional reflectors available prior to this development, each reflector in the sound propagation path caused significant attenuation of the signal, severely limiting the number of reflectors that could be placed in the path.

The solution posed by the present disclosure is a reflector having an aperture that is slightly smaller than the conical propagation beam of the sound wave at the reflector position. The reflector is arranged in a position perpendicular to the beam. Its aperture is coaxial with the beam axis to assure that most of the beam energy passes through it. Reflection of only the periphery of the beam uses energy that is typically not available for subsequent reflection and therefore no significant attenuation occurs due to the reference reflectors.

The drawings illustrate details of a preferred form of the invention. The multi-level probe is shown in a working position within a tank 10, which can be any type of liquid storage tank, whether above ground or below ground. Details of tank 10 are immaterial to an understanding of the present invention.

Figure 1:
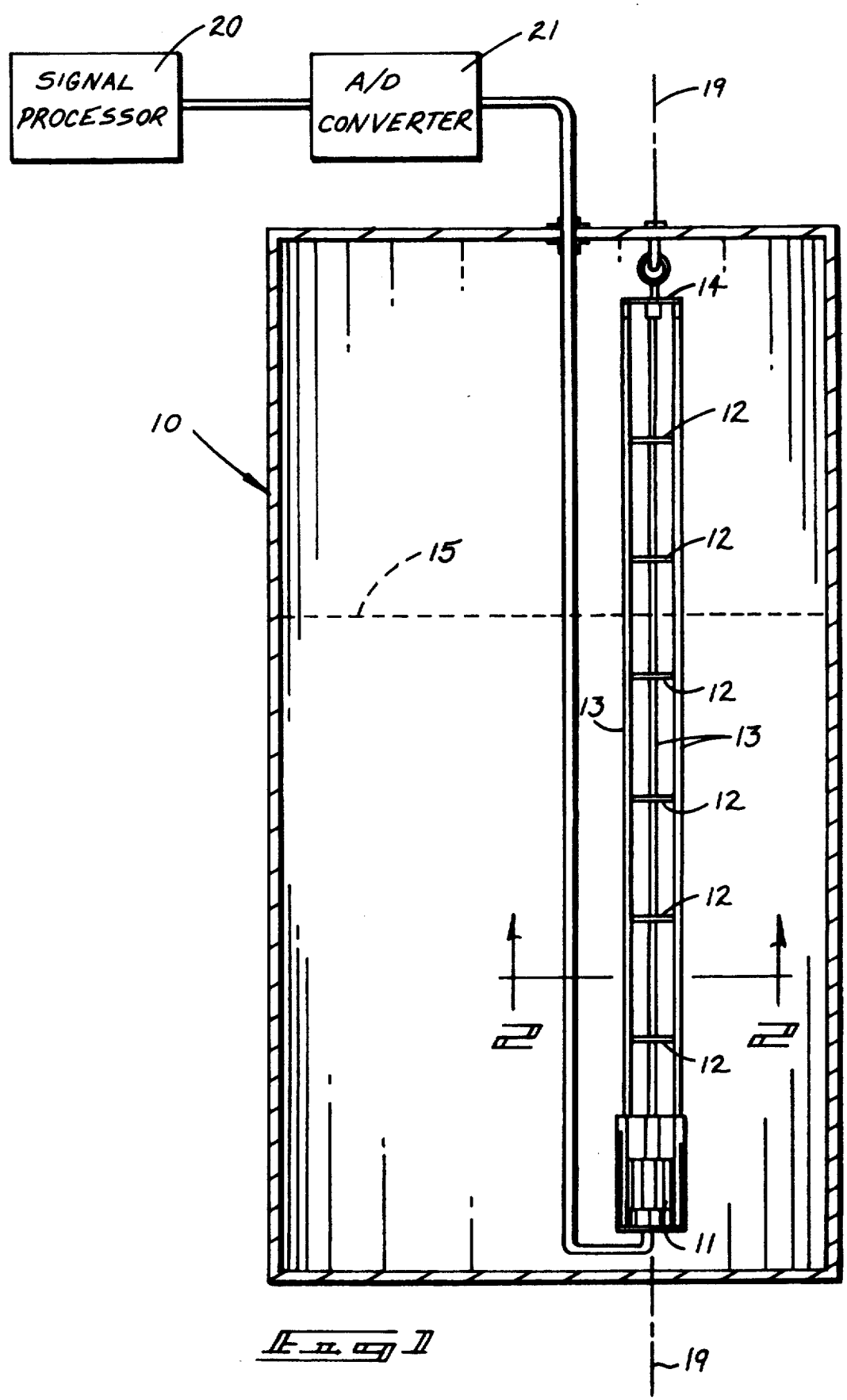
FIG. 1 is a schematic view illustrating the present system in conjunction with a liquid-containing tank.

Tank 10, schematically illustrated in FIG. 1, contains a liquid having a liquid surface illustratively shown at 15. The present multi-level probe can be used for monitoring liquid level, determining liquid volume within tank 10, and measuring temperature and density throughout the liquid within tank 10, as well as measurement of any additional physical properties of the liquid that are a function of the transmission of sonic waves through the liquid.

Figure 2:
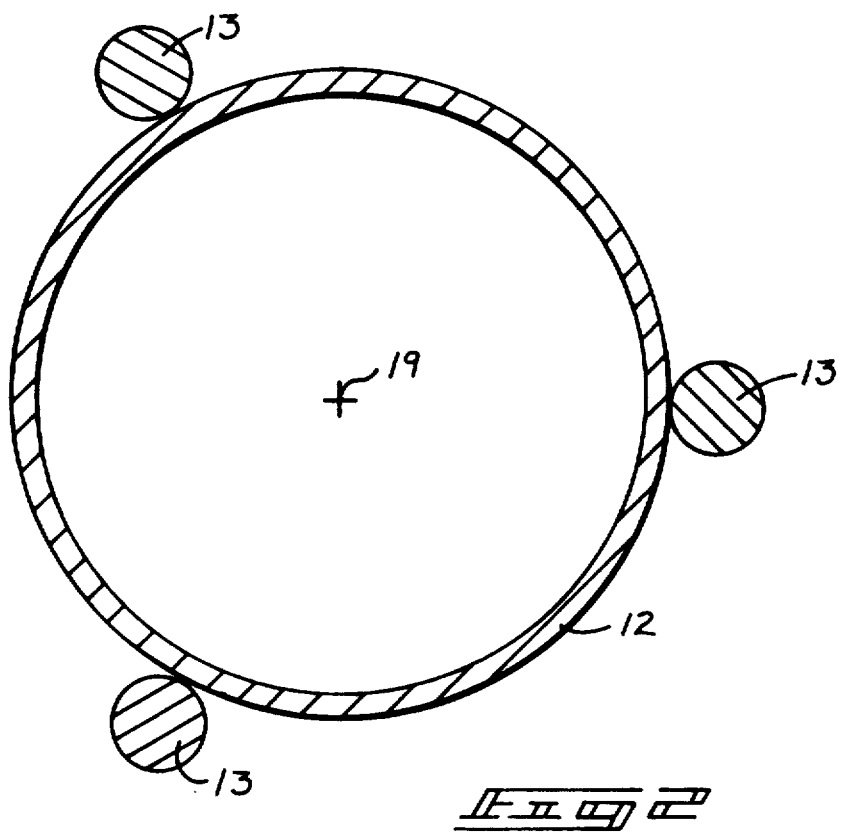
FIG. 2 is an enlarged horizontal section taken across the probe as seen along line 2—2 in FIG. 1.
Figure 3:
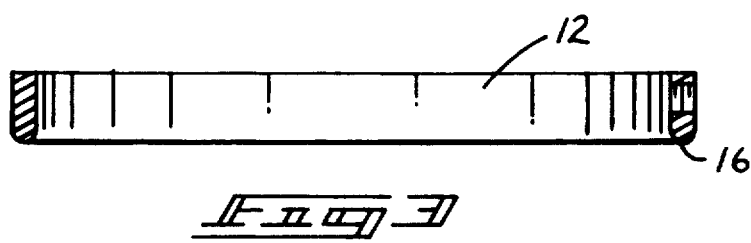
FIG. 3 is an enlarged vertical section through the center of a reflective ring.
Figure 4:
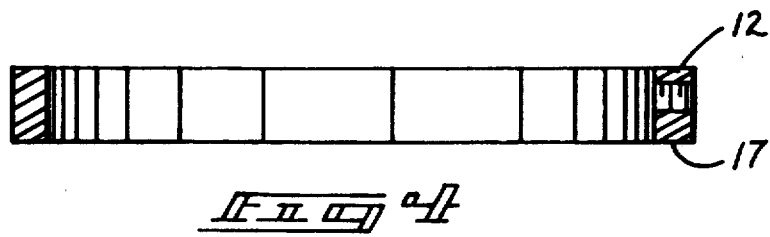
FIG. 4 is similar to FIG. 3, but illustrates a second form of the reflective ring.

The probe essentially comprises a plurality of reflectors 12 that each include an opening or aperture. Reflectors 12 are illustrated as comprising annular rings. The openings at the center of each ring have a periphery surrounded by a reflective surface 16. In FIGS. 1-3, the reflective surface is transversely rounded or toroidal. It can be convex in cross-section, as shown, or concave. Flat reflective surfaces 17, shown in FIG. 4 can also be used, particularly in the upper one-half section of a probe structure. Use of flat reflective surfaces in the lower one-half of the tank 10 has been found to create signals that are difficult to analyze because of the multiple reflections which occur between adjacent reflectors.

Reflectors 12 along the vertical probe have their reflective surfaces 16 (or 17) facing in a common direction about their respective openings. The diameter of each opening is selected to reflect the edges of a beam of ultrasonic energy transmitted along a central reference axis 19 extending vertically along the center of the probe while it is in use.

The reflectors 12 are carried on support means shown as a plurality of posts 13 fixed to the respective reflectors 12 by any suitable fastening technique. The posts 13 position reflectors 12 at preselected transverse locations with their respective openings arranged about reference axis 19 (see FIGS. 1 and 2). The peripheries of the openings in reflectors 12 are preferably coaxially positioned along the common reference axis 19.

A sonic transducer 11 is fixed between the support posts 13 at their lowermost ends. It faces upwardly and is centered along axis 19. Transducer 11 is used for transmitting sonic energy outwardly in a conically shaped beam centered about the reference axis 19 and for producing output signals as a function of reflected sonic energy returned to the transducer as an echo.

The multi-level probe is completed by a hanger 14 secured to the upper ends of posts 13 for suspending the probe as a unit within a tank 10, as schematically shown in FIG. 1.

The transversely rounded reflective surfaces 16 have been found to significantly decrease the problem of multiple echoes or reflections between the reflectors 12 and transducer 11. In normal use, the multi-level probe will extend from the bottom of tank 10 to its top, with the transducer 11 directly adjacent the bottom tank surface. The use of rounded reflective surfaces 16 is of primary importance in the lower one-half of the multi-level probe. Multiple reflections from the reflectors 12 at the upper half of the multi-level probe are not a problem, since they present signals having an apparent range exceeding the height of the tank, and can therefore be readily discarded by signal processing software techniques.

Distortion of the received signals at transducer 11 will also occur unless the reflector thickness is a multiple of an odd number of ¼ of the sonic energy wave length in the medium comprising the reflector (¼, ¾, 5/4, 7/4, etc.). This is not a concept novel to the present disclosure, but is important in practicing the invention because the basic echo concept will not otherwise work well in practice due to timing errors associated with such distortion.

One must also take into account the well-known effects of both acoustic reflection amplitude and distortion in the reflectors based on their thickness (in wavelength). In finalizing the probe design following experimentation, the use of ¾ wavelength thickness for the reflectors was selected to maximize reflectance and minimize transmission of the bursts of sonic energy.

The peripheral diameter of each opening in the respective reflectors 12 affects the acoustic energy available to the subsequent reflectors. A large diameter reflector aperture, relative to the acoustic beam diameter striking it, will reflect a very limited amount of the transmitted sonic energy. A small diameter reflector aperture, again relative to the beam diameter, will upset the wave front as it passes through the reflector 12 by introducing an interference pattern resulting from edge effects.

The annular reflective surfaces 16 have been generally described as being "transversely rounded." By this it is meant that the surfaces have curvature in directions transverse to the reference axis 19 about the surface areas in the path of the transmitted sonic energy from transducer 11. The curvature shape of the impacted reflective areas is not considered to be critical, so long as they are not flat and perpendicular to axis 19. The reflective surface 16 can be a section of a torus, or can be parabolic or hyperbolic, oval, ellipsoidal or can have other curvatures that are not specifically definable by geometric terms. As previously mentioned, the curved surfaces can be either concave or convex, or a combination of both.

The sonic transducer 11 is controlled by a suitable signal processor 20 (FIG. 1) such as a conventional microprocessor. An A/D converter 21 provides the signal processor with digital values representing the instantaneous amplitude of reflected ultrasonic signals impinging on transducer 11. The signal processor 20 is operatively connected to sonic transducer 11 for converting the resulting output signals to data indicative of a measured physical condition.

A significant feature of the invention is a novel method of processing the reflected signal measurements to determine the time required for a sonic burst emitted by the transducer 11 to propagate to a reflector 12 and then back to the transducer 11.

The transducer 11 emits a sinusoidal burst of known period T and phase for a predetermined duration. The radian frequency of the transmitted burst in radians/second can be represented by $\omega$. The transmitted burst can then be approximated by the equation:

$$Y_t = k \cos(\omega t),$$

$y_t$ being the instantaneous intensity of the transmitted burst at time t, $\omega = 2\pi/T$ being the frequency of the transmitted burst, and k being a modulating function that is zero until the start of the burst, increases in amplitude over the next several cycles, remains constant for the duration of the burst, and then returns to zero.

In the preferred embodiment $\omega = 2\pi$ Mrad/sec = 1 Mhz. The period T of each cycle is $1/(2\pi\omega) = 1$ $\mu$s. The radian frequency of the transmitted burst is preferably between 5 Mrad/sec and 10 Mrad/sec.

Each burst will propagate upwardly through the liquid until it encounters the first reflector 12. As explained above, the outer portions or fringe of each burst of sonic energy is partially reflected and echoes back to the transducer 11 as a reflected burst of sonic energy. The remaining burst energy continues to propagate upwardly until it encounters the next reflector 12. The outer fringe of burst energy is again partially reflected back to transducer 11. In a similar fashion, each succeeding reflector 12 sequentially reflects a fringe portion of the burst energy back to transducer 11. Burst energy reaching the top of the liquid level is reflected by the liquid surface 15.

To enable the signal processor 20 to detect each reflected burst, it is necessary that the end of each reflected burst reach transducer 11 before the beginning of the next reflected burst. Accordingly, the duration $t_b$ of the originally transmitted burst must be shorter than the difference in propagation times between two successive reflected signals.

In the preferred embodiment, the duration of the burst is 100 $\mu$s or 100 cycles the first time a burst is sent. Subsequent bursts can be less than 100 $\mu$s (approximately 20 $\mu$s) because the approximate locations of the reflective surfaces will have already been determined from the first burst.

After the brust transmission, the process or 20 repetitively measures the instantaneous amplitude of the reflected energy at the sonic transducer. These values are stored within the signal processor's memory for later reference. As will be explained, it is important to perform all measurements on the reflected signals at a fixed frequency which is an integral multiple of the sinusoidal burst frequency.

In the preferred embodiment, the reflected signals are measured at a rate of 8 MegaSamples/second.

FIG. 5 shows a time-based plot of a transmitted burst 31 and a corresponding plot of the reflected burst 33. While actual transmission of the transmitted burst 31 does not extend past $t_b$, a dashed line 32 shows the same burst 31 extended in time over the period of its reflection.

Reflected burst 33 impinges on transducer 11 after transmission of burst 31 has ended. The signal processor 20 periodically samples the instantaneous amplitude of the reflected burst energy 33 beginning at $t = t_0$, and continues sampling at a constant sampling frequency. The consecutively measured values are referred to as $x_i$, $x_{i+1}, \ldots, x_{i+n}$, where $n+1$ represents the total number of values measured.

To determine the propagation time $t_p$ of the output signals, the following method first determines the phase angle $\theta$ between transmitted burst energy represented by reference numeral 32 in FIG. 5 and the reflected burst energy represented by reference numeral 33. It then determines the number of full cycles $\beta$ of the transmitted burst energy 31 and its time extension 32 from the leading cycle of the transmitted burst 31 to the leading cycle of the reflected burst 33. From these values, the propagation time $t_p$ can be calculated by the equation:

$$t_p = T(\beta + \theta/2\pi).$$

The signal processor 20 first analyzes the measured values of instantaneous amplitude x to determine the approximate beginning of the reflected burst 33. Since $t_p$ is known within an approximate range, the signal processor's analysis can be confined to values measured during this time range. It then selects a contiguous group of values $x_i$ through $x_{i+n}$, measured at $t_i$ through $t_{i+n}$, which represent samples from this portion of the reflected burst energy 33. $\theta$ is then determined by the following equation, which was derived using the method of least squares:

$$\theta = \tan^{-1}\left( \frac{\sum\limits_{j=i}^{i+n} x_j\sin(\omega t_j) \sum\limits_{j=i}^{i+n} \cos^2(\omega t_j) - \sum\limits_{j=i}^{i+n} x_j\cos(\omega t_j) \sum\limits_{j=i}^{i+n} \sin(\omega t_j)\cos(\omega t_j)}{\sum\limits_{j=i}^{i+n} x_j\cos(\omega t_j) \sum\limits_{j=i}^{i+n} \sin^2(\omega t_j) - \sum\limits_{j=i}^{i+n} x_j\sin(\omega t_j) \sum\limits_{j=i}^{i+n} \sin(\omega t_j)\cos(\omega t_j)} \right)$$

where $t_j$ represents the time when the value $x_j$ was measured.

In practice, n is chosen so that the measurements represent an integral number of burst periods. Stated differently, the values of the instantaneous amplitude of the reflected energy at the source transducer 11 are taken as being measured for a duration of cT, where c is an integer. Assuming that n+1 equals the total number of instantaneous amplitude values measured, n+1=cm, where m equals the number of samples taken during each period T. As a consequence:

$$\sum_{j=1}^{i+n} \sin(\omega t_j)\cos(\omega t_j) = 0$$

and $$\sum_{j=i}^{i+n} \cos^2(\omega t_j) = \sum_{j=1}^{i+n} \sin^2(\omega t_j)$$

so that the above formula simplifies to:

$$\theta = \tan^{-1}\left( \frac{\sum\limits_{j=i}^{i+n} x_j\sin(\omega t_j)}{\sum\limits_{j=i}^{i+n} x_j\cos(\omega t_j)} \right)$$

The quadrant of $\theta$ can be determined by usual methods from the signs of the numerator and denominator in the equation and used to determine the phase angle.

It has been observed that determination of $\theta$ in this manner yields results with a much finer resolution than the sampling interval. In facts, digital sampling theory states the $\theta$ can be measured exactly if $x_j$ were known exactly and the number of samples per period is greater than two.

In the preferred embodiment, for example, the A/D sample rate is only 8 MegaSamples/second, while the reflected burst has a frequency of 1 Mhz. This means that only 8 measurements are taken during each cycle of the reflected burst 33—one measurement for each 45 degrees of the reflected burst. But even with this relatively low sample rate, and with $x_j$ measured with 8 bits of resolution, $\theta$ can be calculated to an accuracy of better than 1 degree. This accuracy is maintained even when n is less than or equal to 40. In addition, the method provides a high degree to immunity to noise, is not dependent upon amplitude thresholds, and may be performed with relatively few simple calculations due to an the presence of an integral number of cycles in the sample interval.

Once $\theta$ is known, the signal processing device can make an accurate determination of $\beta$. Beginning at a point which is known to precede reception of the reflected burst, successive values of $x_a$, which would closely correspond to a positive ro negative peak of the reflected burst 33, can be analyzed to determine which value of $x_a$ corresponds with the beginning of a series of alternately positive and negative values. The value $x_a$ occurs at time $t_a$ and $\beta$ can then be calculated as:

$$\beta = \text{integer}(t_a/T).$$

As one familiar in the art will recognize, various additional methods of noise reduction may be utilized. For example, multiple bursts may be transmitted, with the resulting corresponding measurements of the reflected burst being accumulated and averaged.

Signal processing techniques can also be used to determine the leading cycle of the reflected burst. Once $\theta$ is known, the signal processor can calculate when each peak of the reflected burst was received at the transducer. It can then determine which of the measurements of x fall closest in time of positive and negative peaks of the reflected burst. These values, in the preferred embodiment, will occur at every fourth value of x.

Beginning at a value of x which is known to precede the leading cycle of the reflected burst, the following equation is calculated for each consecutive value of $x_a$:

$$Z_a = \sum_{j=a-k}^{a+k} x_j \cos(\omega t_j + \theta)$$

where k is equal to the number of samples per period of the burst divided by two. The value $t_j$ is the time t when the measurement $x_j$ was taken.

The signal processor can then analyze the values of $Z_a$ produced by the above calculation, looking for a series of alternately positive and negative values. The beginning of this series will correspond to the leading cycle of the reflected burst.

Once $\beta$ has been determined in this manner, the propagation time of the output signals $t_p$ can be directly calculated by the equation:

$$t_p = T(\beta + \theta/2\pi).$$

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

We claim:

1. An apparatus for sonic measurement of physical conditions within a liquid, comprising:
   a vertical support;
   sonic transducer means for transmitting a beam of sonic energy upwardly along the support and for receiving downwardly reflected portions of the beam; and
   a plurality of transverse reflectors spaced apart from one another along an axis on the support, the reflectors each including an opening arranged coaxially about the axis for permitting passage through the opening of a substantial percentage of a conically shaped beam of sonic energy directed upwardly along the axis while also downwardly reflecting outer portions of the beam.

2. An apparatus for sonic measurement of physical conditions within a liquid, comprising:

a support;

a plurality of transverse reflectors spaced apart from one another along an axis on the support, the reflectors each including an opening arranged about the axis for permitting passage through the opening of a substantial percentage of a conically shaped beam of sonic energy directed along the axis while also reflecting outer portions of the beam, at least some of the openings being bounded by a periphery including a transversely rounded reflective surface.

3. An apparatus for sonic measurement of physical conditions within a liquid, comprising:

a support;

a plurality of transverse reflectors spaced aprat from one another along an axis on the support, the reflectors each including an opening arranged about the axis for permitting passage through the opening of a substantial percentage of a conically shaped beam of sonic energy directed along the axis while also reflecting outer portions of the beam, at least some of the openings being bounded by a circular periphery coaxially positioned about the axis and including a transversely rounded reflective surface.

4. An apparatus for sonic measurement of physical conditions within a liquid, comprising:

a support;

a plurality of transverse reflectors spaced apart from one another along an axis on the support, the reflectors each including an opening arranged about the axis for permitting passage through the opening of a substantial percentage of a conically shaped beam of sonic energy directed along the axis while also reflecting outer portions of the beam, each reflector being an annular ring having a toroidal surface area serving as it reflective surface.

5. An apparatus for sonic measurement of physical conditions within a liquid, comprising:

sonic transducer means for transmitting energy in an upwardly-directed, conically shaped beam centered about a reference axis and for producing output signals as a function of reflected energy returned downwardly to the sonic transducer means;

a plurality of reflectors each having an opening centered about the reference axis and bounded by a peripheral reflective surface, the reflectors being transversely positioned at preselected locations along the reference axis with their reflective surfaces directed downwardly toward the sonic transducer means for permitting passage through the openings of a substantial percentage of a conically shaped beam of sonic energy directed along the reference axis by the sonic transducer means while also downwardly reflecting outer portions of the beam; and support means carrying both the sonic transducer means and the reflectors for positioning the reflectors above the sonic transducer means in vertical alignment along the reference axis.

6. An apparatus for sonic measurement of physical conditions within a liquid, comprising:

sonic transducer means for transmitting energy in a conically shaped beam centered about a reference axis and for producing output signals as a function of reflected energy returned to the sonic transducer means; and a plurality of reflectors each having an opening centered about the reference axis and bounded by a peripheral reflective surface, the reflectors being transversely positioned at preselected locations along the reference axis with their reflective surfaces directed toward the sonic transducer means for permitting passage through the openings of a substantial percentage of a conically shaped beam of sonic energy directed along the reference axis by the sonic transducer means while also reflecting outer portions of the beam, the reflective surface of each reflector being transversely rounded.

7. An apparatus for sonic measurement of physical conditions within a liquid, comprising:

sonic transducer means for transmitting energy in a conically shaped beam centered about a reference axis and for producing output signals as a function of reflected energy returned to the sonic transducer means;

a plurality of reflectors each having an opening centered about the reference axis and bounded by a peripheral reflective surface, the reflectors being transversely positioned at preselected locations along the reference axis with their reflective surfaces directed toward the sonic transducer means for permitting passage through the openings of a substantial percentage of a conically shaped beam of sonic energy directed along the reference axis by the sonic transducer means while also reflecting outer portions of the beam; and signal processor means for:

repetitively measuring the value of the instantaneous amplitude of the reflected energy at the sonic transducer, the values of the instantaneous amplitude of the reflected energy being represented by $x_i, x_{i+1}, \ldots, x_{i+n}$, where $n+1$ represents the total number of values measured; and determining the phase angle $\theta$ between the transmitted energy and the reflected energy by the equation:

$$\theta = \tan^{-1}\left(\frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)}\right)$$

where $t_j$ represents the time when the value $x_j$ was measured and $\omega = 2\pi/T$ is the radian frequency of the transmitted energy.

8. An apparatus for sonic measurement of physical conditions within a liquid, comprising:

sonic transducer means for transmitting energy in a conically shaped beam centered about a reference axis and for producing output signals as a function of reflected energy returned to the sonic transducer means;

a plurality of reflectors each having an opening centered about the reference axis and bounded by a peripheral reflective surface, the reflectors being transversely positioned at preselected locations along the reference axis with their reflective surfaces directed toward the sonic transducer means for permitting passage through the openings of a substantial percentage of a conically shaped beam of sonic energy directed along the reference axis by the sonic transducer means while also reflecting outer portions of the beam; and signal processor means for:

repetitively measuring the value of the instantaneous amplitude of the reflected energy at the sonic transducer, the values of the instantaneous amplitude of the reflected energy being represented by $x_i, x_{i+1}, \ldots, x_{i+n}$, where $n+1$ represents the total number of values measured; and determining the phase angle $\theta$ between the transmitted energy and the reflected energy by the equation:

$$\theta = \tan^{-1}\left(\frac{\sum_{j=i}^{i+n} x_j\sin(\omega t_j) \sum_{j=i}^{i+n} \cos^2(\omega t_j) - \sum_{j=i}^{i+n} x_j\cos(\omega t_j) \sum_{j=i}^{i+n} \sin(\omega t_j)\cos(\omega t_j)}{\sum_{j=i}^{i+n} x_j\cos(\omega t_j) \sum_{j=i}^{i+n} \sin^2(\omega t_j) - \sum_{j=i}^{i+n} x_j\sin(\omega t_j) \sum_{j=i}^{i+n} \sin(\omega t_j)\cos(\omega t_j)}\right)$$

where $t_j$ represents the time when the value $x_j$ was measured and $\omega = 2\pi/T$ is the radian frequency of the transmitted energy; and determining the quadrant of $\theta$ from the signs of the numerator and denominator in the equation used to determine the phase angle.

9. An apparatus for sonic measurement of physical conditions within a liquid, comprising:

sonic transducer means for transmitting energy in a conically shaped beam centered about a reference axis and for producing output signals as a function of reflected energy returned to the sonic transducer means;

a plurality of reflectors each having an opening centered about the reference axis and bounded by a peripheral reflective surface, the reflectors being transversely positioned at preselected locations along the reference axis with their reflective surfaces directed toward the sonic transducer means for permitting passage through the openings of a substantial percentage of a conically shaped beam of sonic energy directed along the reference axis by the sonic transducer means while also reflecting outer portions of the beam; and signal processor means for:

repetitively measuring the value of the instantaneous amplitude of the reflected energy at the sonic transducer, the values of the instantaneous amplitude of the reflected energy being represented by $x_i, x_{i+1}, \ldots, x_{i+n}$, where $n+1$ represents the total number of values measured; and determining the phase angle $\theta$ between the transmitted energy and the reflected energy by the equation:

$$\theta = \tan^{-1}\left(\frac{\sum_{j=i}^{i+n} x_j\sin(\omega t_j) \sum_{j=i}^{i+n} \cos^2(\omega t_j) - \sum_{j=i}^{i+n} x_j\cos(\omega t_j) \sum_{j=i}^{i+n} \sin(\omega t_j)\cos(\omega t_j)}{\sum_{j=i}^{i+n} x_j\cos(\omega t_j) \sum_{j=i}^{i+n} \sin^2(\omega t_j) - \sum_{j=i}^{i+n} x_j\sin(\omega t_j) \sum_{j=i}^{i+n} \sin(\omega t_j)\cos(\omega t_j)}\right)$$

where $t_j$ represents the time when the value $x_j$ was measured and $\omega = 2\pi/T$ is the radian frequency of the transmitted energy;

determining the quadrant of $\theta$ from the signs of the numerator and denominator in the equation used to determine the phase angle;

determining the number of integral periods T which elapsed from the first peak of the transmitted energy to the first peak of the reflected energy, the number of integral periods being designated as $\beta$; and calculating the propagation time of the output signals by the equation:

$$t_p = T(\beta + \theta/2\pi).$$

10. An apparatus for sonic measurement of physical conditions within a liquid, comprising:

sonic transducer means for transmitting energy in a conically shaped beam centered about a reference axis and for producing output signals as a function of reflected energy returned to the sonic transducer means;

a plurality of reflectors each having an opening centered about the reference axis and bounded by a peripheral reflective surface, the reflectors being transversely positioned at preselected locations along the reference axis with their reflective surfaces directed toward the sonic transducer means for permitting passage through the openings of a substantial percentage of a conically shaped beam of sonic energy directed along the reference axis by the sonic transducer means while also reflecting outer portions of the beam; and signal processor means for:

repetitively measuring the value of the instantaneous amplitude of the reflected energy at the source transducer for a duration of cT, where c is an integer, the values of the instantaneous amplitude of the reflected energy being represented by $x_i, x_{i+1}, \ldots, x_{i+n}$, where $n+1$ represents the total number of values measured and $n+1 = cm$, where m equals the number of samples taken during each period T; and determining the phase angle $\theta$ between the transmitted energy and the reflected energy by the equation:

$$\theta = \tan^{-1}\left(\frac{\sum_{j=i}^{i+n} x_j \sin(\omega t_j)}{\sum_{j=i}^{i+n} x_j \cos(\omega t_j)}\right)$$

where $t_j$ represents the time when the value $x_j$ was measured and $\omega = 2\pi/T$ is the radian frequency of the transmitted energy.

11. An apparatus for sonic measurement of physical conditions with a liquid, comprising:

sonic transducer means for transmitting energy in a conically shaped beam centered about a reference axis for producing output signals as a function of reflected energy returned to the sonic transducer means;

a plurality of reflectors each having an opening centered about the reference axis and bounded by a peripheral reflective surface, the reflectors being transversely positioned at preselected locations along the reference axis with their reflective surfaces directed toward the sonic transducer means for permitting passage through the openings of a substantial percentage of a conically shaped beam of sonic energy directed along the reference axis by the sonic transducer means while also reflecting outer portions of the beam; and signal processor means for:

repetitively measuring the value of the instantaneous amplitude of the reflected energy at the source transducer for a duration of cT, where c is an integer, the values of the instantaneous amplitude of the reflected energy being by $x_i, x_{i+1}, \ldots, x_{i+n}$, where $n+1$ represents the total number of values measured and $n+1=cm$, where m equals the number of samples taken during each period T;

determining the phase angle $\theta$ between the transmitted energy and the reflected energy by the equation:

$$\theta = \tan^{-1}\left(\frac{\sum_{j=i}^{i+n} x_j \sin(\omega t_j)}{\sum_{j=i}^{i+n} x_j \cos(\omega t_j)}\right)$$

where $t_j$ represents the time when the value $x_j$ was measured and $\omega = 2\pi/T$ is the radian frequency of the transmitted energy; and determining the quadrant of $\theta$ from the signs of the numerator and denominator in the equation used to determine the phase angle.

12. An apparatus for sonic measurement of physical conditions within a liquid, comprising:

sonic transducer means for transmitting energy in a conically shaped beam centered about a reference axis and for producing output signals as a function of reflected energy returned to the sonic transducer means;

a plurality of reflectors each having an opening centered about the reference axis and bounded by a peripheral reflective surface, the reflectors being transversely positioned at preselected locations along the reference axis with their reflective surfaces directed toward the sonic transducer means for permitting passage through the openings of a substantial percentage of a conically shaped beam of sonic energy directed along the reference axis by the sonic transducer means while also reflecting outer portions of the beam; and signal processor means for:

repetitively measuring the value of the instantaneous amplitude of the reflected energy at the source transducer for a duration of cT, where c is an integer, the values of the instantaneous amplitude of the reflected energy being represented by $x_i, x_{i+1}, \ldots, x_{i+n}$, where $n+1$ represents the total number of values measured and $n+1=cm$, where m equals the number of samples taken during each period T;

determining the phase angle $\theta$ between the transmitted energy and the reflected energy by the equation:

$$\theta = \tan^{-1}\left(\frac{\sum_{j=i}^{i+n} x_j \sin(\omega t_j)}{\sum_{j=i}^{i+n} x_j \cos(\omega t_j)}\right)$$

where $t_j$ represents the time when the value $x_j$ was measured and $\omega = 2\pi/T$ is the radian frequency of the transmitted energy;

determining the quadrant of $\theta$ from the signs of the numerator and denominator in the equation used to determine the phase angle;

determining the number of integral periods T which elapsed from the first peak of the transmitted energy to the first peak of the reflected energy, the number of integral periods being designated as $\beta$; and calculating the propagation time of the output signals by the equation:

$$t_p = T(\beta + \theta/2\pi).$$

13. An apparatus for sonic measurement of physical conditions within a liquid, comprising:

an elongated upright support;

sonic transducer means mounted to the lower end of the support for transmitting energy upwardly in a conically shaped beam centered about a reference axis and for producing output signals as a function of reflected energy returned to the transducer means as an echo; and a plurality of reflector rings mounted to the support at preselected spaced locations along the reference axis relative to the sonic transducer means, the reflector rings each including a reflective surface surrounding an opening formed through it and centered about the reference axis, the reflector rings being positioned along the support with their reflective surfaces facing downwardly toward the sonic transducer means for permitting passage through the openings of a substantial percentage of a conically shaped beam of sonic energy directed along the reference axis by the sonic transducer means while also downwardly reflecting outer portions of the beam.

14. An apparatus for sonic measurement of physical conditions within a liquid, comprising:

an elongated support;
sonic transducer means mounted to the support for transmitting energy in a conically shaped beam centered about a reference axis and for producing output signals as a function of reflected energy returned to the transducer means as an echo; and
a plurality of reflector rings mounted to the support at preselected spaced locations along the reference axis relative to the sonic transducer means, the reflector rings each including a reflective surface surrounding an opening formed through it and centered about the reference axis, the reflector rings being positioned along the support with their reflective surfaces facing toward the sonic transducer means for permitting passage through the openings of a substantial percentage of a conically shaped beam of sonic energy directed along the reference axis by the sonic transducer means while also reflecting outer portions of the beam, the reflective surfaces of the reflector rings being transversely rounded.

15. An apparatus for sonic measurement of physical conditions within a liquid, comprising:
an elongated support;
sonic transducer means mounted to the support for transmitting energy in a conically shaped beam centered about a reference axis and for producing output signals as a function of reflected energy returned to the transducer means as an echo; and
a plurality of reflector rings mounted to the support at preselected spaced locations along the reference axis relative to the sonic transducer means, the reflector rings each including a reflective surface surrounding an opening formed through it and centered about the reference axis, the reflector rings being positioned along the support with their reflective surfaces facing toward the sonic transducer means for permitting passage through the openings of a substantial percentage of a conically shaped beam of sonic energy directed along the reference axis by the sonic transducer means while also reflecting outer portions of the beam;
the support comprising a plurality of elongated posts fixed to the reflector rings;
the reflector rings being arranged along the reference axis in equally spaced parallel positions and with each reflector ring being perpendicular to the reference axis.

16. The apparatus of claim 13, further comprising:
signal processor means operatively connected to the sonic transducer means for converting the output signals to data indicative of a measured physical condition.

17. An apparatus for sonic measurement of physical conditions within a liquid, comprising:
an elongated support;
sonic transducer means mounted to the support for transmitting energy in a conically shaped beam centered about a reference axis and for producing output signals as a function of reflected energy returned to the transducer means as an echo;
a plurality of reflector rings mounted to the support at preselected spaced locations along the reference axis relative to the sonic transducer means, the reflector rings each including a reflective surface surrounding an opening formed through it and centered about the reference axis, the reflector rings being positioned along the support with their reflective surfaces facing toward the sonic transducer means for permitting passage through the openings of a substantial percentage of a conically shaped beam of sonic energy directed along the reference axis by the sonic transducer means while also reflecting outer portions of the beam; and
signal processor means for:
repetitively measuring the value of the instantaneous amplitude of the reflected energy at the sonic transducer, the values of the instantaneous amplitude of the reflected energy being represented by $x_i, x_{i+1}, \ldots, x_{i+n}$, where $n+1$ represents the total number of values measured; and
determining the phase angle $\theta$ between the transmitted energy and the reflected energy by the equation:

$$\theta = \tan^{-1}\left( \frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)} \right)$$

where $t_j$ represents the time when the value $x_j$ was measured and $\omega = 2\pi/T$ is the radian frequency of the transmitted energy.

18. An appartus for sonic measurement of physical conditions within a liquid, comprising:
an elongated support;
sonic transducer means mounted to the support for transmitting energy in a conically shaped beam centered about a reference axis and for producing output signals as a function of reflected energy returned to the transducer means as an echo;
a plurality of reflector rings mounted to the support at preselected spaced locations along the reference axis relative to the sonic transducer means, the reflector rings each including a reflective surface surrounding an opening formed through it and centered about the reference axis, the reflector rings being positioned along the support with their reflective surfaces facing toward the sonic transducer means for permitting passage through the openings of a substantial percentage of a conically shaped beam of sonic energy directed along the reference axis by the sonic transducer means while also reflecting outer portions of the beam; and
signal processor means for:
repetitively measuring the value of the instantaneous amplitude of the reflected burst at the source transducer, the values of the reflected burst's instantaneous amplitude being represented by $x_i, x_{i+1}, \ldots, x_{i+n}$, where $n+1$ represents the total number of values measured;
determining the phase angle $\theta$ between the transmitted burst and the reflected burst by the equation:

$$\theta = \tan^{-1}\left(\frac{\sum_{j=i}^{i+n} x_j\sin(\omega t_j) \sum_{j=i}^{i+n} \cos^2(\omega t_j) - \sum_{j=i}^{i+n} x_j\cos(\omega t_j) \sum_{j=i}^{i+n} \sin(\omega t_j)\cos(\omega t_j)}{\sum_{j=i}^{i+n} x_j\cos(\omega t_j) \sum_{j=i}^{i+n} \sin^2(\omega t_j) - \sum_{j=i}^{i+n} x_j\sin(\omega t_j) \sum_{j=i}^{i+n} \sin(\omega t_j)\cos(\omega t_j)}\right)$$

where $t_j$ represents the time when the value $x_j$ was measured and $\omega = 2\pi/T$ is the radian frequency of the transmitted burst; and determining the quadrant of $\theta$ from the signs of the numerator and denominator in the equation used to determine the phase angle.

19. An apparatus for sonic measurement of physical conditions within a liquid, comprising:

an elongated support;

sonic transducer means mounted to the support for transmitting energy in a conically shaped beam centered about a reference axis and for producing output signals as a function of reflected energy returned to the transducer means as an echo;

a plurality of reflector rings mounted to the support at preselected spaced locations along the reference axis relative to the sonic transducer means, the reflector rings each including a reflective surface surrounding an opening formed through it and centered about the reference axis, the reflector rings being positioned along the support with their reflective surfaces facing toward the sonic transducer means for permitting passage through the openings of a substantial percentage of a conically shaped beam of sonic energy directed along the reference axis by the sonic transducer means while also reflecting outer portions of the beam; and signal processor means for:

repetitively measuring the value of the instantaneous amplitude of the reflected burst at the source transducer, the values of the reflected burst's instantaneous amplitude being represented by $x_i, x_{i+1}, \ldots, x_{i+n}$, where $n+1$ represents the total number of values measured;

determining the phase angle $\theta$ between the transmitted burst and the reflected burst by the equation:

20. An apparatus for sonic measurement of physical conditions within a liquid, comprising:

an elongated support;

sonic transducer means mounted to the support for transmitting energy in a conically shaped beam centered about a reference axis and for producing output signals as a function of reflected energy returned to the transducer means as an echo;

a plurality of reflector rings mounted to the support at preselected spaced locations along the reference axis relative to the sonic transducer means, the reflector rings each including a reflective surface surrounding an opening formed through it and centered about the reference axis, the reflector rings being positioned along the support with their reflective surfaces facing toward the sonic transducer means for permitting passage through the openings of a substantial percentage of a conically shaped beam of sonic energy directed along the reference axis by the sonic transducer means while also reflecting outer portions of the beam; and signal processor means for:

repetitively measuring the value of the instantaneous amplitude of the reflected energy at the source transducer for a duration of $cT$, where c is an integer, the values of the instantaneous amplitude of the reflected energy being represented by $x_i, x_{i+1}, \ldots, x_{i+n}$, where $n+1$ represents the total number of values measured and $n+1=cm$, where m equals the number of samples taken during each period T; and determining the phase angle $\theta$ between the transmitted energy and the reflected energy by the equation:

$$\theta = \tan^{-1}\left(\frac{\sum_{j=i}^{i+n} x_j\sin(\omega t_j) \sum_{j=i}^{i+n} \cos^2(\omega t_j) - \sum_{j=i}^{i+n} x_j\cos(\omega t_j) \sum_{j=i}^{i+n} \sin(\omega t_j)\cos(\omega t_j)}{\sum_{j=i}^{i+n} x_j\cos(\omega t_j) \sum_{j=i}^{i+n} \sin^2(\omega t_j) - \sum_{j=i}^{i+n} x_j\sin(\omega t_j) \sum_{j=i}^{i+n} \sin(\omega t_j)\cos(\omega t_j)}\right)$$

where $t_j$ represents the time when the value $x_j$ was measured and $\omega = 2\pi/T$ is the radian frequency of the transmitted burst;

determining the quadrant of $\theta$ from the signs of the numerator and denominator in the equation used to determine the phase angle;

determining the number of integral periods T which elapsed from the first peak of the transmitted energy to the first peak of the reflected energy, the number of integral periods being designated as $\beta$; and calculating the propagation time of the output signals by the equation:

$t_P = T(\beta + \theta/2\pi)$.

$$\theta = \tan^{-1}\left(\frac{\sum_{j=i}^{i+n} x_j\sin(\omega t_j)}{\sum_{j=i}^{i+n} x_j\cos(\omega t_j)}\right)$$

where $t_j$ represents the time when the value $x_j$ was measured and $\omega = 2\pi/T$ is the radian frequency of the transmitted energy.

21. An apparatus for sonic measurement of physical conditions within a liquid, comprising:

an elongated support;

sonic transducer means mounted to the support for transmitting energy in a conically shaped beam centered about a reference axis and for producing output signals as a function of reflected energy returned to the transducer means as an echo;

a plurality of reflector rings mounted to the support at preselected spaced locations along the reference axis relative to the sonic transducer means, the reflector rings each including a reflective surface surrounding an opening formed through it and centered about the reference axis, the reflector rings being positioned along the support with their reflective surfaces facing toward the sonic transducer means for permitting passage through the openings of a substantial percentage of a conically shaped beam of sonic energy directed along the reference axis by the sonic transducer means while also reflecting outer portions of the beam; and signal processor means for:

repetitively measuring the value of the instantaneous amplitude of the reflected energy at the source transducer for a duration of cT, where c is an integer, the values of the instantaneous amplitude of the reflected every being represented by $x_i$, $x_{i+i+1}$, ..., $x_{i+n}$, where n+1 represents the total number of values measured and n+1=cm, where m equals the number of samples taken during each period T; and determining the phase angle $\theta$ between the transmitted energy and the reflected energy by the equation:

$$\theta = \tan^{-1}\left(\frac{\sum_{j=i}^{i+n} x_j\sin(\omega t_j) \sum_{j=i}^{i+n} \cos^2(\omega t_j) - \sum_{j=i}^{i+n} x_j\cos(\omega t_j) \sum_{j=i}^{i+n} \sin(\omega t_j)\cos(\omega t_j)}{\sum_{j=i}^{i+n} x_j\cos(\omega t_j) \sum_{j=i}^{i+n} \sin^2(\omega t_j) - \sum_{j=i}^{i+n} x_j\sin(\omega t_j) \sum_{j=i}^{i+n} \sin(\omega t_j)\cos(\omega t_j)}\right)$$

where $t_j$ represents the time when the value $x_j$ was measured and $\omega = 2\pi/T$ is the radian frequency of the transmitted energy;

determining the quadrant of $\theta$ from the signs of the numerator and denominator in the equation used to determine the phase angle;

determining the number of integral periods T which elapsed from the first peak of the transmitted energy to the first peak of the reflected energy, the number of integral periods being designated as $\beta$; and calculating the propagation time of the output signals by the equation:

$t_p = T(\beta + \theta/2\pi)$.

23. An apparatus for sonic measurement of physical conditions within a liquid, comprising:

transducer means for transmitting a sinusoidal burst of known period T and phase for a predetermined duration;

reflector means for reflecting the transmitted burst back toward the source transducer as a reflected burst; and signal processor means for:

repetitively measuring, at a rate greater than 2/T, the value of the instantaneous amplitude of the reflected burst at the source transducer, the values of the reflected burst's instantaneous amplitude being represented by $x_i$, $x_{i+1}$, ..., $x_{i+n}$, where n+1 represents the total number of values measured; and determining the phase angle $\theta$ between the transmitted burst and the reflected burst by the equation:

--- of values measured and n+1=cm, where m equals the number of samples taken during each period T; and determining the phase angle $\theta$ between the transmitted energy and the reflected energy by the equation:

$$\theta = \tan^{-1}\left(\frac{\sum_{j=i}^{i+n} x_j\sin(\omega t_j)}{\sum_{j=i}^{i+n} x_j\cos(\omega t_j)}\right)$$

where $t_j$ represents the time when the value $x_j$ was measured and $\omega = 2\pi/T$ is the radian frequency of the transmitted energy; and determining the quadrant of $\theta$ from the signs of the numerator and denominator in the equation used to determine the phase angle.

22. An apparatus for sonic measurement of physical conditions within a liquid, comprising:

an elongated support;

sonic transducer means mounted to the support for transmitting energy in a conically shaped beam centered about a reference axis and for producing output signals as a function of reflected energy returned to the transducer means as an echo;

a plurality of reflector rings mounted to the support at preselected spaced locations along the reference axis relative to the sonic transducer means, the reflector rings each including a reflective surface surrounding an opening formed through it and centered about the reference axis, the reflector $$\theta = \tan^{-1}\left(\frac{\sum_{j=i}^{i+n} x_j\sin(\omega t_j) \sum_{j=i}^{i+n} \cos^2(\omega t_j) - \sum_{j=i}^{i+n} x_j\cos(\omega t_j) \sum_{j=i}^{i+n} \sin(\omega t_j)\cos(\omega t_j)}{\sum_{j=i}^{i+n} x_j\cos(\omega t_j) \sum_{j=i}^{i+n} \sin^2(\omega t_j) - \sum_{j=i}^{i+n} x_j\sin(\omega t_j) \sum_{j=i}^{i+n} \sin(\omega t_j)\cos(\omega t_j)}\right)$$

where $t_j$ represents the time when the value $x_j$ was measured and $\omega = 2\pi/T$ is the radian frequency of the transmitted burst.

24. An apparatus for sonic measurement of physical conditions within a liquid, comprising:

transducer means for transmitting a sinusoidal burst of known period T and phase for a predetermined duration;

reflector means for reflecting the transmitted burst back toward the source transducer as a reflected burst; and signal processor means for:

repetitively measuring the value of the instantaneous amplitude of the reflected energy at the source transducer for a duration of cT, where c is an integer, the values of the instantaneous amplitude of the reflected energy being represented by $x_i, x_{i+1}, \ldots, x_{i+n}$, where $n+1$ represents the total number of values measured and $n+1 = cm$, where m equals the number of samples taken during each period T; and determining the phase angle $\theta$ between the transmitted burst and the reflected burst by the equation:

$$\theta = \tan^{-1}\left(\frac{\sum_{j=i}^{i+n} x_j\sin(\omega t_j)}{\sum_{j=i}^{i+n} x_j\cos(\omega t_j)}\right)$$

where $t_j$ represents the time when the value $x_j$ was measured and $\omega = 2\pi/T$ is the radian frequency of the transmitted burst.

25. A method of analyzing the propagation of a sinusoidal burst from a source transducer to a reflecting surface and back to the source transducer, comprising the steps of:

transmitting a sinusoidal burst of known period T and phase from a source transducer for a predetermined duration, the transmitted burst being approximated by the equation:

$y_t = k \cos(\omega t)$, where $y_t$ is the instantaneous intensity of the transmitted burst at time t, $\omega = 32\pi/T$ is the frequency of the transmitted burst, and k is a modulating function that is zero until the start of the burst, increases in amplitude over the next several cycles, remains constant for the duration of the burst, and then returns to zero;

reflecting at least part of the transmitted burst back toward the source transducer from a reflective surface as a reflected burst;

repetitively measuring the value of the instantaneous amplitude of the reflected burst at the source transducer, the values of the reflected burst's instantaneous amplitude being represented by $x_i, x_{i+1}, \ldots, x_{i+n}$, where $n+1$ represents the total number of values measured; and determining the phase angle $\theta$ between the transmitted burst and the reflected burst by the equation:

$$\theta = \tan^{-1}\left(\frac{\sum_{j=i}^{i+n} x_j\sin(\omega t_j) \sum_{j=i}^{i+n} \cos^2(\omega t_j) - \sum_{j=i}^{i+n} x_j\cos(\omega t_j) \sum_{j=i}^{i+n} \sin(\omega t_j)\cos(\omega t_j)}{\sum_{j=i}^{i+n} x_j\cos(\omega t_j) \sum_{j=i}^{i+n} \sin^2(\omega t_j) - \sum_{j=i}^{i+n} x_j\sin(\omega t_j) \sum_{j=i}^{i+n} \sin(\omega t_j)\cos(\omega t_j)}\right)$$

where $t_j$ represents the time when the value $x_j$ was measured and $\omega = 2\pi/T$ is the radian frequency of the transmitted burst.

26. The method of claim 25, further comprising the following additional step:

determining the quadrant of $\theta$ from the signs of the numerator and denominator in the equation used to determine the phase angle.

27. The method of claim 25, further comprising the following additional steps:

determining the quadrant of $\theta$ from the signs of the numerator and denominator in the equation used to determine the phase angle;

determining the number of integral periods T which elapsed from the first peak of the transmitted energy to the first peak of the reflected energy, the number of integral periods being designated as $\beta$; and calculating the propagation time of the output signals by the equation:

$t_p = T(\beta + \theta/2\pi)$.

28. The method of claim 26 wherein the propagation time $t_p$ is determined for multiple consecutive reflected bursts that are reflections, from multiple reflective surfaces, of a single transmitted burst.

29. A method of analyzing the propagation of a sinusoidal burst from a source transducer to a reflecting surface and back to the source transducer, comprising the steps of:

transmitting a sinusoidal burst of known period T and phase from a source transducer for a predetermined duration, the transmitted burst being approximated by the equation:

$y_t = k \cos(\omega t)$, where $y_t$ is the instantaneous intensity of the transmitted burst at time t, $\omega = 2\pi/T$ is the frequency of the transmitted burst, and k is a modulating function that is zero until the start of the burst, increases in amplitude over the next several cycles, remains constant for the duration of the burst, and then returns to zero;

reflecting at least part of the transmitted burst back toward the source transducer from a reflective surface as a reflected burst;

repetitively measuring the value of the instantaneous amplitude of the reflected energy at the source transducer for a duration of cT, where c is an integer, the values of the instantaneous amplitude of the reflected energy being represented by $x_i$, $x_{i+1}$, ..., $x_{i+n}$, where n+1 represents the total number of values measured and n+1=cm, where m equals the number of samples taken during each period T; and determining the phase angle $\theta$ between the transmitted burst and the reflected burst by the equation:

$$\theta = \tan^{-1}\left(\frac{\sum_{j=i}^{i+n} x_j \sin(\omega t_j)}{\sum_{j=i}^{i+n} x_j \cos(\omega t_j)}\right)$$

where $t_j$ represents the time when the value $x_j$ was measured and $\omega = 2\pi/T$ is the radian frequency of the transmitted burst.

30. The method of claim 29, further comprising the following additional step:

determining the quadrant of $\theta$ from the signs of the numerator and denominator in the equation used to determine the phase angle.

31. The method of claim 29, further comprising the following additional steps:

determining the quadrant of $\theta$ from the signs of the numerator and denominator in the equation used to determine the phase angle;

determining the number of integral periods T which elapsed from the first peak of the transmitted energy to the first peak of the reflected energy, the number of integral periods being designated as $\beta$; and calculating the propagation time of the output signals by the equation:

$$t_P = T(\beta + \theta/2\pi).$$

32. The method of claim 30 wherein the propagation time $t_P$ is determined for multiple consecutive reflected bursts that are reflections, from multiple reflective surfaces, of a single transmitted burst.

* * * * *

UNITED STATES PATENT AND TRADEMARK OFFICE
CERTIFICATE OF CORRECTION

PATENT NO.   : 5,121,340
DATED        : June 9, 1992
INVENTOR(S)  : Eric Campbell; Gaylon Campbell; Jeff Norton; and Art Heers It is certified that error appears in the above-identified patent and that said Letters Patent is hereby corrected as shown below:

Columns 7 and 8,
Lines 1-7, delete the mathematical equation, and insert the following corrected equation which includes the previously missing parenthesis at the end of the sine term just before the cosine term in the rightmost denominator $$\theta = \tan^{-1}\left[\frac{\sum_{j=i}^{i+n}x_j\sin(\omega t_j)\sum_{j=i}^{i+n}\cos^2(\omega t_j)-\sum_{j=i}^{i+n}x_j\cos(\omega t_j)\sum_{j=i}^{i+n}\sin(\omega t_j)\cos(\omega t_j)}{\sum_{j=i}^{i+n}x_j\cos(\omega t_j)\sum_{j=i}^{i+n}\sin^2(\omega t_j)-\sum_{j=i}^{i+n}x_j\sin(\omega t_j)\sum_{j=i}^{i+n}\sin(\omega t_j)\cos(\omega t_j)}\right]$$

Columns 9 and 10, claim 7,
Lines 55-59, delete the mathematical equation, and insert the following corrected equation which includes the previously missing parenthesis at the end of the sine term just before the cosine term in the rightmost denominator:

$$\theta = \tan^{-1}\left[\frac{\sum_{j=i}^{i+n}x_j\sin(\omega t_j)\sum_{j=i}^{i+n}\cos^2(\omega t_j)-\sum_{j=i}^{i+n}x_j\cos(\omega t_j)\sum_{j=i}^{i+n}\sin(\omega t_j)\cos(\omega t_j)}{\sum_{j=i}^{i+n}x_j\cos(\omega t_j)\sum_{j=i}^{i+n}\sin^2(\omega t_j)-\sum_{j=i}^{i+n}x_j\sin(\omega t_j)\sum_{j=i}^{i+n}\sin(\omega t_j)\cos(\omega t_j)}\right]$$

UNITED STATES PATENT AND TRADEMARK OFFICE
CERTIFICATE OF CORRECTION

PATENT NO.   : 5,121,340
DATED        : June 9, 1992
INVENTOR(S)  : Eric Campbell; Gaylon Campbell; Jeff Norton; and Art Heers It is certified that error appears in the above-identified patent and that said Letters Patent is hereby corrected as shown below:

Columns 11 and 12, claim 8,
Lines 37-40, delete the mathematical equation, and insert the following corrected equation which includes the previously missing parenthesis at the end of the sine term just before the cosine term in the rightmost denominator:

$$\theta = \tan^{-1}\left[\frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)}\right]$$

Columns 11 and 12, claim 9,
Lines 10-13, delete the mathematical equation, and insert the following corrected equation which includes the previously missing parenthesis at the end of the sine term just before the cosine term in the rightmost denominator:

$$\theta = \tan^{-1}\left[\frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)}\right]$$

UNITED STATES PATENT AND TRADEMARK OFFICE
CERTIFICATE OF CORRECTION

PATENT NO. : 5,121,340
DATED : June 9, 1992
INVENTOR(S) : Eric Campbell; Gaylon Campbell; Jeff Norton; and Art Heers It is certified that error appears in the above-identified patent and that said Letters Patent is hereby corrected as shown below:

Columns 15 and 16, claim 17,
Lines 29-32, delete the mathematical equation, and insert the following corrected equation which includes the previously missing parenthesis at the end of the sine term just before the cosine term in the rightmost denominator:

$$\theta = \tan^{-1}\left[\frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)}\right]$$

Columns 17 and 18, claim 18,
Lines 1-6, delete the mathematical equation, and insert the following corrected equation which includes the previously missing parenthesis at the end of the sine term just before the cosine term in the rightmost denominator:

$$\theta = \tan^{-1}\left[\frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)}\right]$$

UNITED STATES PATENT AND TRADEMARK OFFICE
CERTIFICATE OF CORRECTION

PATENT NO.    : 5,121,340
DATED         : June 9, 1992
INVENTOR(S)   : Eric Campbell; Gaylon Campbell; Jeff Norton; and Art Heers It is certified that error appears in the above-identified patent and that said Letters Patent is hereby corrected as shown below:

Columns 17 and 18, claim 19,
Lines 47-50, delete the mathematical equation, and insert the following corrected equation which includes the previously missing parenthesis at the end of the sine term just before the cosine term in the rightmost denominator:

$$\theta = \tan^{-1}\left[\frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)}\right]$$

Columns 19 and 20, claim 22,
Lines 26-30, delete the mathematical equation, and insert the following corrected equation which includes the previously missing parenthesis at the end of the sine term just before the cosine term in the rightmost denominator:

$$\theta = \tan^{-1}\left[\frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)}\right]$$

UNITED STATES PATENT AND TRADEMARK OFFICE
CERTIFICATE OF CORRECTION

PATENT NO. : 5,121,340
DATED : June 9, 1992
INVENTOR(S) : Eric Campbell; Gaylon Campbell; Jeff Norton; and Art Heers It is certified that error appears in the above-identified patent and that said Letters Patent is hereby corrected as shown below:

Columns 21 and 22, claim 23,
Lines 1-5, delete the mathematical equation, and insert the following corrected equation which includes the previously missing parenthesis at the end of the sine term just before the cosine term in the rightmost denominator:

$$\theta = \tan^{-1}\left[\frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)}\right]$$

UNITED STATES PATENT AND TRADEMARK OFFICE
CERTIFICATE OF CORRECTION

PATENT NO. : 5,121,340
DATED : June 9, 1992
INVENTOR(S) : Eric Campbell; Gaylon Campbell; Jeff Norton; and Art Heers It is certified that error appears in the above-identified patent and that said Letters Patent is hereby corrected as shown below:

Columns 21 and 22, claim 25,
Lines 22-25, delete the mathematical equation, and insert the following corrected equation which includes the previously missing parenthesis at the end of the sine term just before the cosine term in the rightmost denominator:

$$\theta = \tan^{-1}\left[\frac{\sum_{j=i}^{i+n} x_j \sin(\omega t_j) \sum_{j=i}^{i+n} \cos^2(\omega t_j) - \sum_{j=i}^{i+n} x_j \cos(\omega t_j) \sum_{j=i}^{i+n} \sin(\omega t_j)\cos(\omega t_j)}{\sum_{j=i}^{i+n} x_j \cos(\omega t_j) \sum_{j=i}^{i+n} \sin^2(\omega t_j) - \sum_{j=i}^{i+n} x_j \sin(\omega t_j) \sum_{j=i}^{i+n} \sin(\omega t_j)\cos(\omega t_j)}\right]$$

Signed and Sealed this

Twelfth Day of February, 2002

Attest:

Attesting Officer

JAMES E. ROGAN
Director of the United States Patent and Trademark Office